(12) United States Patent
Shaw et al.

(10) Patent No.: US 8,362,028 B2
(45) Date of Patent: *Jan. 29, 2013

(54) PSEUDOBASE BENZO[C]PHENANTHRIDINES WITH IMPROVED EFFICACY, STABILITY AND SAFETY

(75) Inventors: Kenneth Shaw, Weston, CT (US); Mingbao Zhang, Stamford, CT (US); Amy F. T. Arnsten, Bethany, CT (US)

(73) Assignee: Yale University, New Haven, CT (US)

( * ) Notice: Subject to any disclaimer, the term of this patent is extended or adjusted under 35 U.S.C. 154(b) by 605 days.

This patent is subject to a terminal disclaimer.

(21) Appl. No.: 12/418,823

(22) Filed: Apr. 6, 2009

(65) Prior Publication Data
US 2010/0256164 A1 Oct. 7, 2010
US 2012/0264766 A9 Oct. 18, 2012

Related U.S. Application Data

(63) Continuation of application No. 11/831,498, filed on Jul. 31, 2007, now Pat. No. 7,531,550.

(60) Provisional application No. 60/834,375, filed on Jul. 31, 2006.

(51) Int. Cl.
A61K 31/44 (2006.01)
A61K 31/535 (2006.01)
C07D 221/18 (2006.01)

(52) U.S. Cl. ............ 514/280; 514/298; 514/232.8; 546/42

(58) Field of Classification Search .............. None
See application file for complete search history.

(56) References Cited

U.S. PATENT DOCUMENTS
3,912,740 A 10/1975 Zee-Cheng et al.
2005/0070565 A1* 3/2005 Arnsten et al. ............. 514/283
2008/0076781 A1* 3/2008 Shaw et al. ............. 514/255.05

OTHER PUBLICATIONS

Assem et al. "Further Alkaloids From Bark of Fagara Mayu" Planta Medica 1983, 48(2), pp. 77-80. Abstract Only.
Sharma et al. "Toddalidimerine, a Dimeric Benzophenanthridine Alkaloid from Toddalia Aslatica" Phyochemistry, 1981, vol. 20, No. 12, pp. 2781-2783.
Stermitz et al. "Some Structural Relationships Among Cytotoxic and Antitumor Benzophenanthidine Alkaloid Derivatives" Journal of Medicinal Chemistry, 1973, vol. 16, No. 8, pp. 939-940.
Waterman et al. "The Biochemical Systematics of Fagaropsis Angolensis and its Significance in the Rutales" Biochemical Systematics and Ecology, 1981, vol. 9, No. 1, pp. 45-51.

* cited by examiner

Primary Examiner — Bong-Sook Baek
(74) Attorney, Agent, or Firm — Cantor Colburn LLP

(57) ABSTRACT

Pseudobase benzo[c]phenanthridines and the pharmaceutically acceptable salts thereof of Formula I

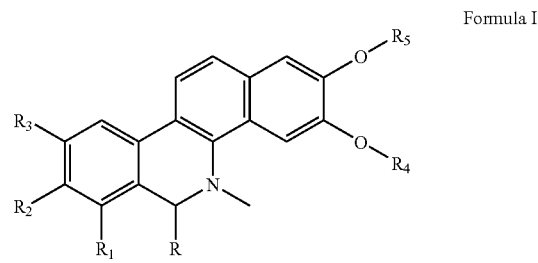

Formula I are provided herein. The variables R, $R_1$, $R_2$, $R_3$, and $R_4$ are defined herein. Certain pseudobase benzo[c]phenanthridines provided herein act as prodrugs, targeting the parent benzo[c]phenanthridinium alkaloid to hydrophilic or hydrophobic regions in the body. Pharmaceutical compositions comprising a pseudobase benzo[c]phenanthridine and a carrier, excipient, or diluent are provided herein. Methods of treating or preventing microbial, fungal and or viral infections and methods of treating diseases and disorders responsive to protein kinase C modulation, topoisomerase I, and/or topoisomerase II modulation are also provided.

1 Claim, No Drawings

PSEUDOBASE BENZO[C]PHENANTHRIDINES WITH IMPROVED EFFICACY, STABILITY AND SAFETY

This application is a continuation of U.S. Non-provisional application Ser. No. 11/831,498, filed Jul. 31, 2007, now U.S. Pat. No. 7,531,550, which claims priority from U.S. Provisional Application No. 60/834,375, filed Jul. 31, 2006.

FIELD OF THE INVENTION

Pseudobase benzo[c]phenanthridines are provided herein. Certain pseudobase benzo[c]phenanthridines provided herein act as prodrugs, targeting the parent benzo[c]phenanthridinium alkaloid to hydrophilic or hydrophobic regions in the body. Pharmaceutical compositions comprising a pseudobase benzo[c]phenanthridine and a carrier, excipient, or diluent are provided herein. Methods of treating or preventing microbial infections and methods of treating diseases and disorders responsive to protein kinase C modulation, topoisomerase I and/or II modulation, are also provided.

BACKGROUND

The benzo[c]phenanthridinium alkaloids are a class of naturally occurring pharmaceutically active compounds that have been known for centuries. Well-known benzo[c]phenathridinium alkaloids include sanguinarine, chelerythrine, nitidine, and fagaronine.

Pharmaceutical utility for several of the benzo[c]phenantridinium alkaloids has been demonstrated. Sanguinarine and chelerythrine possess protein kinase C (PKC) antagonist activity, anti-microbial activity, and anti-fungal properties. These compounds are the major constituents of an extract used to treat gum disease and reduce plaque. Sanguinaria extract (containing approx. 50% sanguinarine and 25% chelerythrine) has been utilized in a commercial dental rinse and toothpaste. Nitidine and fagaronine have anti-cancer activity and have been investigated in clinical trials. Cardiovascular toxicity has limited the development of Nitidine as an anti-cancer drug.

Generally, phenanthridinium alkaloids have strong cytotoxic activity and are active as protein kinase C, topisomerase I, and/or topoisomerase II inhibitors. Chelerythrine is unique in that it does not stabilize the DNA adduct as do the others in this class.

The benzo[c]phenanthridinium alkaloids all possess a common phenathridine core and additionally have in common a quartenary nitrogen. The quartenary nitrogen and molecular planarity are postulated to be responsible for the rich pharmacology associated with these alkaloids as reduction to the dihydro analog results in a significant reduction of pharmacological activities.

The quaternary nitrogen imparts inherent chemical reactivity into these alkaloids. Nucleophiles can readily add to the adjacent carbon to create a neutral pseudobase. Water forms an unstable adduct with chelerythrine that can be seen in NMR studies. Additionally, 6-methoxy-5,6-dihydrochelerytherine and 6-ethoxy-5,6-dihydrochelerytherine (Artarine) have been reported as byproducts formed during the isolation of chelerythrine from blood root utilizing methanol and ethanol extractions.

The pseudoalcoholates (methoxy and ethoxy) of sanguinarine and chelerythrine are more potent antimicrobial agents than the parent alkaloids of these compounds. The methoxy, ethoxy and cyano sanguinarine psuedobases are about two times more potent than sanguinarine in antimicrobial assays. A crude mixture of chelerythrine methoxy and ethoxy pseudoalcoholates, also demonstrated improved efficacy over the parent in anti-microbial assays. It has been postulated that these pseudoalcoholates may act as prodrugs for their parent phenanthridinium alkaloid, however, this hypothesis is not general as the pseudoalcoholates (methanol and ethanol) of nitidine are less active in leukemia assays than the parent, nitidine. The lipophilic pseudobases are neutral, and more capable of passive diffusion across cell membranes and the blood/brain barrier than the parent alkaloid. Once inside the cell or the appropriate microenvironment in membranes it is likely that the pseudobase reverts to the parent benzo[c] phenanthridinium alkaloid resulting in increased potency and or safety. Polar pseudobase phenanthridines may be synthesized that offer activity to receptors, enzymes and cell types in the blood with greater selectivity than the parent phenanthridinium alkaloid. In certain instances prodrugs of active pharmaceutical agents have highly desirable properties. For example prodrugs may provide superior efficacy and safety. Thus prodrugs of phenanthridinium alkaloids are highly desirable. The invention provides such compounds and also provides further advantages, which are described herein.

SUMMARY OF THE INVENTION

A first embodiment provides a compound of Formula I

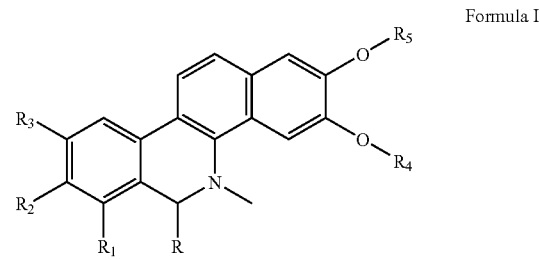

Formula I or a pharmaceutically acceptable salt thereof wherein:

$R_1$ and $R_2$ are each independently hydrogen, halogen, hydroxy, $C_1$-$C_3$alkyl, $C_1$-$C_6$alkoxy, $C_1$-$C_6$alkoxycarbonyl, or $C_2$-$C_6$alkanoyloxy; or $R_1$ and $R_2$ are joined by a —O—$CH_2$—O— group.

$R_3$ is hydrogen or methoxy.

$R_4$ and $R_5$ are independently methyl or hydrogen; or $R_4$ and $R_5$ are joined to form a 5-membered heterocycloalkyl ring containing no additional heteroatoms.

R is (i) a group of the formula -AB, where A is —$NR_6$—, —O—,
—$NR_6$(C=O)—, —S(O)$_m$—, —S(O)$_m$$NR_6$—, —$NR_6$S(O)$_m$—, —$NR_6$(S=O)$NR_7$—, —O(C=O)—, —$NR_6$(C=O)$NR_7$—, where m is 0, 1, or 2 and B is $C_1$-$C_8$alkyl, $C_2$-$C_8$alkenyl, $C_2$-$C_8$alkynyl, $C_2$-$C_4$alkanoyl, (carbocycle)$C_0$-$C_2$alkyl or (heterocycle)$C_0$-$C_2$alkyl, each of which is substituted with from 0 to 4 substituents independently chosen from halogen, hydroxy, amino, cyano, $C_1$-$C_4$alkyl, $C_1$-$C_4$alkoxy, mono- or di-($C_1$-$C_4$alkyl)amino, $C_1$-$C_2$haloalkyl, and $C_1$-$C_2$haloalkoxy, with the proviso that B is not $C_1$-$C_2$alkyl when A is —O—.

Or, R is (ii)

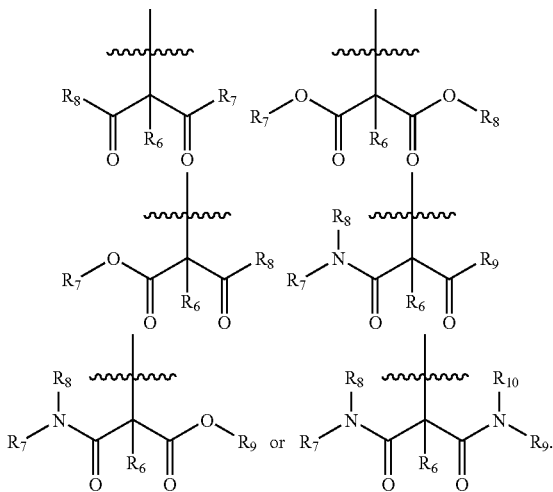

Or, R is (iii) a 5-membered heteroaryl group having at least one nitrogen ring member, and 0, 1, or 2 additional ring members independently chosen from N, O, and S, wherein the 5-membered heteroaryl group is attached via a nitrogen atom and is substituted with 0 to 3 substituents independently chosen from halogen, hydroxy, amino, cyano, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_6$, $R_7$, $R_8$, $R_9$, and $R_{10}$ are each independently hydrogen, or $C_1$-$C_8$alkyl, $C_2$-$C_8$alkenyl, $C_2$-$C_8$alkynyl, $C_2$-$C_4$alkanoyl, ($C_3$-$C_{10}$cycloalkyl)$C_0$-$C_8$alkyl or (heterocycloalkyl)$C_0$-$C_8$alkyl, each of which is substituted with from 0 to 4 substituents independently chosen from halogen, hydroxy, amino, cyano, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

Also provided herein are pharmaceutical compositions comprising a compound or pharmaceutically acceptable salt of Formula I together with a pharmaceutically acceptable carrier, diluent, or excipient.

Improved methods of treating or preventing diseases that can be effectively treated with benzo[c]phenanthridinium alkaloids are provided herein. A method of treating or preventing a microbial infection in a mammal comprising administering an effective amount of a compound of Formula I to the mammal is provided herein. Methods of treating a patient suffering from bipolar disorder, the negative symptoms of schizophrenia, microbial infection, fungal infection, viral infection, cancer, AIDS, Rheumatoid Arthritis comprising administering to the patient an effective amount of a compound or salt of Formula I are also provided herein.

DETAILED DESCRIPTION OF THE INVENTION

Chemical Description and Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

Formula I includes all subformulae thereof For example Formula I includes compounds of Formulae II, and 1 to 6 disclosed herein.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the compounds described herein. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

All pharmaceutically acceptable forms of compounds of Formula I are included herein. Pharmaceutically acceptable forms include pharmaceutically acceptable salts, hydrates, solvates, crystal forms, polymorphs, chelates, non-covalent complexes, esters, clathrates, and mixtures of such compounds. Pharmaceutically acceptable salts are a preferred pharmaceutically acceptable form of compounds of Formula I.

"Pharmaceutically acceptable salts" include derivatives of the disclosed compounds wherein the parent compound is modified by making non-toxic acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

Certain compounds are described herein using a general formula that includes variables, e.g. R, $R_1R_5$, A, and B. Unless otherwise specified, each variable defined independently of each other variable in the formula. Thus, if a group is said to be substituted, e.g. with 0-2 R*, then said group may be substituted with up to two R* groups and R* at each occurrence is selected independently. Also, combinations of substituents and/or variables are permissible only if such combinations result in stable compounds. A stable compound is a compound sufficiently robust to survive isolation from a reaction mixture and subsequent formulation into an effective therapeutic agent.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates.

A dash ("-") that is not between two letters or symbols is used to indicate a point of attachment for a substituent. For example, —$(CH_2)C_3$-$C_8$cycloalkyl is attached through carbon of the methylene ($CH_2$) group.

By "Alkyl" is meant both branched and straight chain saturated aliphatic hydrocarbon groups, having the specified number of carbon atoms, generally from 1 to about 8 carbon atoms. When $C_0$-$C_n$ alkyl is used herein in conjunction with another group, for example, (carbocycle)$C_0$-$C_4$ alkyl, the indicated group, in this case a carbocycle, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, iso-propyl, n-butyl, 3-methylbutyl, t-butyl, n-pentyl, and sec-pentyl. Preferred alkyl groups are those having from 1 to about 6 carbon atoms, or from 1 to about 4 carbons atoms e.g. $C_1$-$C_6$ and $C_1$-$C_4$ alkyl groups.

"Alkenyl" as used herein, indicates a straight or branched hydrocarbon chain comprising one or more unsaturated carbon-carbon bonds, which may occur in any stable point along the chain. Alkenyl groups described herein typically have from 2 to about 8 carbons atoms. Preferred alkenyl groups are alkenyl groups having from 2 to about 6 or from 2 to about 4 carbon atoms, e.g. $C_2$-$C_8$, $C_2$-$C_6$, and $C_2$-$C_4$ alkenyl groups. Examples of alkenyl groups include ethenyl, propenyl, and butenyl groups.

"Alkynyl" indicates hydrocarbon chains of either a straight or branched configuration comprising one or more triple carbon-carbon bonds, which may occur in any stable point along the chain, such as ethynyl and propynyl. Alkynyl groups typically will have 2 to about 8 carbon atoms, more typically 2 to about 6 carbon atoms.

By "alkoxy" is meant an alkyl group as defined above, having the indicated number of carbon atoms, attached through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, 3-methylpentoxy, and the like. Preferred alkoxy groups herein are $C_1$-$C_4$alkoxy groups.

By "alkoxycarbonyl" is meant an ester group of the formula (alkoxy)(C=O)— attached through the carbonyl carbon wherein the alkoxy group has the indicated number of carbon atoms. Thus a C1-C6alkoxycarbonyl group is an alkoxy group having from 1 to about 6 carbon atoms attached through its oxygen to a carbonyl linker.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a C2alkanoyl group is an acetyl group having the formula CH3(C=O)—. "Alkanoyloxy" is an alkanoyl group attached through an oxygen (—O—) bridge.

"Mono- and di-(alkyl)amino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

A "carbocycle" has from 1 to 3 fused, pendant, or spiro rings, containing only carbon ring members. Typically, a carbocyclic ring comprises from 3 to 8 ring members (rings having from 4 or 5 to 7 ring members are recited in certain embodiments) and carbocycles comprising fused, pendant, or spiro rings typically contain from 9 to 14 ring members. Unless otherwise specified, a carbocycle may be a cycloalkyl group (i.e., each ring is saturated), a partially saturated group, or an aryl group (i.e., at least one ring within the group is aromatic). A carbocyclic group may generally be linked via any ring or substituent atom, provided that a stable compound results. When indicated, carbocyclic groups, such as 4- to 7-membered or 5- to 7-membered groups, may be substituted. Representative aromatic carbocycles are phenyl, naphthyl and biphenyl. In certain embodiments preferred carbocycles are carbocycles having a single ring, such as phenyl or 3- to 7-membered cycloalkyl groups.

A carbocycle may be directly attached or attached via an indicated linker group. For example (carbocycle)alkyl substituents are present in some embodiments described herein. In each case "carbocycle" carries the definition set forth above and is covalently bound to the alkyl group, which carries the definition set forth above.

The term "cycloalkyl" is intended to include saturated ring groups, having the specified number of carbon atoms, such as cyclopropyl, cyclobutyl, cyclopentyl, cyclohexyl or cycloheptyl. C3-C10cycloalkyl groups have from 3 to 10 ring members and have 1 or 2 cycloalkyl rings; preferred cycloalkyl groups have 3 to 8 and more preferably 3 to 7 ring members, and have a single ring.

By "(cycloalkyl)alkyl" or (C3-C10cycloalkyl)C0-C8alkyl, is meant a cycloalkyl group as defined above and attached via a single covalent bond (C0alkyl) or via and alkyl bridge having the indicated number of carbon atoms.

The term "halogen" refers to fluorine, chlorine, bromine and iodine.

A "haloalkyl" is a branched or straight-chain alkyl group, substituted with 1 or more halogen atoms (e.g., "C1-C2haloalkyl" groups have from 1 to 2 carbon atoms). Examples of haloalkyl groups include, but are not limited to, mono-, di-, and tri-fluoromethyl; mono-, di-, and tri-chloromethyl; mono-, di-, tri-, tetra-, and penta-fluoroethyl; and mono-, di-, tri-, tetra- and penta-chloroethyl. Typical haloalkyl groups are trifluoromethyl and difluoromethyl.

"Haloalkoxy" indicates a haloalkyl group as defined above attached through an oxygen bridge. "C1-C2haloalkoxy" groups have from 1 to 2 carbon atoms. A typical haloalkoxy is trifluoromethoxy.

A "heterocycle" is a group that comprises at least one ring in which at least one ring atom is a heteroatom (i.e., N, O or S), and the remainder of the ring atoms are carbon. Such a ring is referred to as a heterocyclic ring. Preferably, a heterocyclic ring comprises 1-4 heteroatoms; within certain embodiments 1 or 2 heteroatoms is preferred. A heterocycle generally has from 1 to 3 fused or pendant rings (at least one of which is heterocyclic); a heterocycle preferably has one ring or two fused rings. Typically, each ring contains from 3 to 8 ring members (preferably from 5 to 7 ring members); heterocycles comprising fused or pendant rings typically contain from 9 to 12 ring members. 3- to 10-membered heterocyclic groups that contain 1 heterocyclic ring or 2 fused rings (at least one of which is heterocyclic; for a total of 3 to 10 ring members) are preferred, with 5- to 10-membered heterocyclic groups particularly preferred. Within certain embodiments 5 to 7 membered heterocyclic groups having a single ring and one or two heteroatoms independently chosen from N, O, and S are particularly preferred. Heterocycles may be optionally substituted with one or more substituents as described above for carbocycles. Unless otherwise specified, a heterocycle may be saturated (i.e., heterocycloalkyl, as described above), partially saturated or aromatic (heteroaryl). As used herein the term "heteroaryl" is intended to mean a stable 5- to 7-membered monocyclic or 7- to 10-membered bicyclic heterocyclic aromatic ring structure which consists of carbon atoms and from 1 to 4 heteroatoms independently chosen from N, O and S. It is preferred that the total number of S and O atoms in the heteroaryl group is not more than 1. In the term "heteroarylalkyl," heteroaryl and alkyl are as defined above and the point of attachment is on the alkyl group.

Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

Preferred heteroaryl groups include imidazolyl, pyrrolyl, pyridyl, thiazolyl, pyrazolyl, thiazolyl, isoxazolyl, triazolyl, tetrazolyl, oxadiazolyl, pyrimidinyl and oxazolyl, with pyridyl particularly preferred.

"Heterocycloalkyl" refers to a saturated ring group in which at least one ring member is a heteroatom (i.e., N, S or O), and the remaining ring members are carbon. Heterocycloalkyl groups typically include 3 to 10 rings members, preferably to 8 and more preferably 5 to 7 ring members. Heterocycloalkyl groups typically have from 1 to 3 heteroatoms; preferably not more than one S atom and one O atom are present in a heterocycloalkyl group. Preferred heterocycloalkyl groups are 5 or 6-membered heterocycloalkyl groups, for example morpholinyl, piperidinyl, piperazinyl, thiomorpholinyl, and pyrrolidinyl.

By "(heterocycloalkyl)C0-Cnalkyl" is meant a heterocycloalkyl group as defined above linked via a single covalent bond (C0alkyl) or via an alkyl bridge having the indicated number of carbon atoms.

The term "effective amount" of a compound of this invention means an amount effective, when administered to a mammal, to provide a therapeutic benefit such as an amelioration of symptoms, e.g., an amount effective to decrease the symptoms of a disease. In certain embodiments an effective amount is an amount sufficient to reduce cancer symptoms, decrease the number of detectable cancerous cells in an organism, detectably slow or stop the growth of a cancerous tumor, or more preferably and amount sufficient to shrink a cancerous tumor. In certain circumstances a patient suffering from a disease or disorder may not present symptoms of being affected. Thus a therapeutically effective amount of a compound is also an amount sufficient to prevent a significant increase or significantly reduce the detectable level of disease markers in the patient's blood, serum, or tissues. A significant increase or reduction in the detectable level of disease markers is any detectable change that is statistically significant in a standard parametric test of statistical significance such as Student's T-test, where $p<0.05$.

Pseudobase Benzo[c]Phenanthridines

Appropriate pseudobase of the phenanthridinium alkaloids possesses less toxicity than the parent benzo[c]phenanthridiniums. Pseudobase benzo[c]phenanthridines are useful for "targeting" lipophilic areas, crossing more effectively into the brain or cell to distribute at the desired site of action.

It is believed that pseudobase benzo[c]phenanthridines form when a weak nucleophile that can establish an equilibrium between the pseudobase and parent benzo[c]phenanthridinium alkaloid in the biological medium, is added to a solution of the parent benzo[c]phenanthridinium in a non-polar solvent. Although a general categorization of relative nucleophilic strength of a nucleophile cannot be made, the strength can be correlated somewhat with the basicity of the compound. Therefore, compounds that are weak bases can be described herein as weak nucleophiles. The weak nucleophiles used herein typically have a disassociation or ionization constant [pKa] value of about 4 to about 20 relative to water, preferably about 8 to 20 relative to water, and more preferably about 13 to 18 relative to water.

As long as the derivatization agent is a weak nucleophile, then a useful equilibrium between the pseudobase and phenanthridinium alkaloid parent is established. This equilibrium will be affected by the lipohilicity of the environment, pH and any endogenous nucleophiles that may be present at or around the desired site of action. Thus, certain pseudobase benzo[c]phenanthridines described herein provide a superior efficacy and safety index by targeting the pseudobase to selectively distribute to the site of action and then convert back into the efficacious species. In contrast, the parent phenanthridinium alkaloids distribute in a different manner throughout the body upon administration and are therefore less likely to exhibit a desired profile of efficacy versus toxicity. Certain pseudobase benzo[c]phenanthridines described herein also exhibit different selectivity and improved safety indexes when administered via other routes (i.e. oral, parenteral, transdermal, subcutaneous injection, or suppository, etc). Various oral dosage forms, e.g. enterically coated dosage forms, immediate release, and sustained release dosage forms, also exhibit different selectivity and improved safety indexes when administered.

Examples of Benzo[c]phenanthridinium alkaloids, "parent phenanthridiniums" include the well-characterized compounds, nitidine, fagaronine, chelerythrine, and sanguinarine, all of which have the general formula

TABLE I

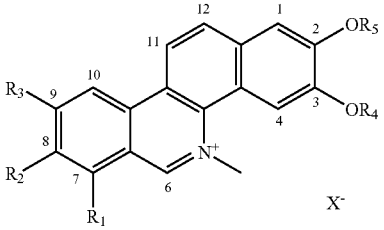

| $R_1$ | $R_2$ | $R_3$ | $R_4$ | $R_5$ | Name |
|---|---|---|---|---|---|
| H | —OCH$_3$ | —OCH$_3$ | | —CH$_2$— | Nitidine |
| H | —OCH$_3$ | —OCH$_3$ | H | —CH$_3$ | Fagaronine |
| —OCH$_3$ | —OCH$_3$ | H | | —CH$_2$— | Chelerythrine |
| —OCH$_2$O— | | H | | —CH$_2$— | Sanguinarine |

Certain preferred compounds of Formula I exhibit greater cell membrane permeability, measured in nm/s than their parent phenanthridinium. Cell membrane permeability can be measured by a standard assay for diffusion across cell membranes such as the Caco-2 assay given in Example 3.

A prediction of cell membrane permeability may also be obtained by LogD measurement.

The n-octanol-water partition coefficient (logP) is the ratio of the concentration of a compound in octanol and in water at equilibrium and at a specified temperature. LogP can be used as a measure of molecular hydrophobicity. Hydrophobicity is known to affect drug absorption and bioavailability. LogP is generally used for non-ionic compounds whereas logD is used to account for ionized and neutral forms of a molecule. LogD is the ratio of the equilibrium concentrations of all species (unionized and ionized) of a molecule in octanol to same species in the water phase at a given temperature, normally 25° C. LogD is defined as logD=$\Sigma[C_i]_{oct}/\Sigma[C_i]_{aq}$, wherein oct is the octanol phase and aq is the water phase. Thus certain preferred compounds of Formula I that possess a greater n-octanol-water partition coefficient (logD) at 25° C. when compared to the parent phenanthridinium are provided herein.

In addition to compounds and pharmaceutically acceptable salts of Formula I, disclosed above in the "Summary of Invention"

Formula I

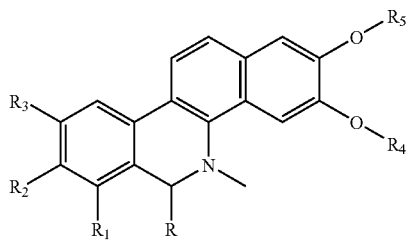

compounds of Formula I in which one or more of the following conditions is met are also provided.

The $R_1$ and $R_2$ Variables

Within certain embodiments R1 and R2 are each independently hydrogen, methyl, or methoxy.

In other embodiments provided herein R1 and R2 are joined by a —OCH2O— group, i.e. to from a compound or salt of Formula II Formula II

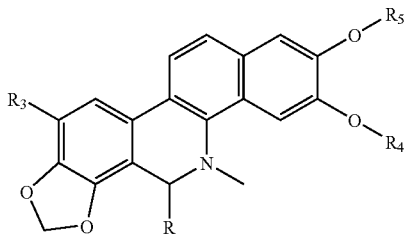

The R Variable

Compounds and salts of Formula I are provided herein in which R is (i) a group of the formula -AB, where A and B carry the definition set forth above for these variables.

Within certain embodiments A is —NR6—, —O—, —NR6(C=O)—, —S(O)2—, or —O(C=O)—.

Also included are embodiments in which B is C1-C6alkyl, (phenyl)C0-C2alkyl, (C3-C7cycloalkyl) C0-C2alkyl, (heterocycloalkyl)C0-C2alkyl, or (heteroaryl)C0-C2alkyl, each of which is substituted with from 0 to 4 substituents independently chosen from halogen, hydroxy, amino, cyano, C1-C4alkyl, C1-C4alkoxy, mono- and di-(C1-C4alkyl)amino, C1-C2haloalkyl, and C1-C2haloalkoxy.

Further included are embodiments in which B is C1-C6alkyl, (phenyl)C0-C2alkyl, (C3-C$_7$cycloalkyl) C$_0$-C$_2$alkyl, (pyrrolidinyl)C$_0$-C$_2$alkyl, (piperidinyl)C$_0$-C$_2$alkyl, (piperazinyl)C$_0$-C$_2$alkyl, (morpholinyl)C$_0$-C$_2$alkyl, (pyridyl)C$_0$-C$_2$alkyl, (thienyl)C$_0$-C$_2$alkyl, (pyrrolyl)C$_0$-C$_2$alkyl, (furanyl)C$_0$-C$_2$alkyl, (imidazolyl)C$_0$-C$_2$alkyl, (thiazolyl)C$_0$-C$_2$alkyl, (pyrimidinyl)C$_0$-C$_2$alkyl, or (pyrazinyl)C$_0$-C$_2$alkyl, each of which is substituted with from 0 to 4 substituents independently chosen from halogen, hydroxy, amino, cyano, C$_1$-C$_4$alkyl, C$_1$-C$_4$alkoxy, mono- and di-(C$_1$-C$_4$alkyl)amino, C$_1$-C$_2$haloalkyl, and C$_1$-C$_2$haloalkoxy.

Compounds and salts of Formula I are provided herein in which R is (ii) a group of the formula

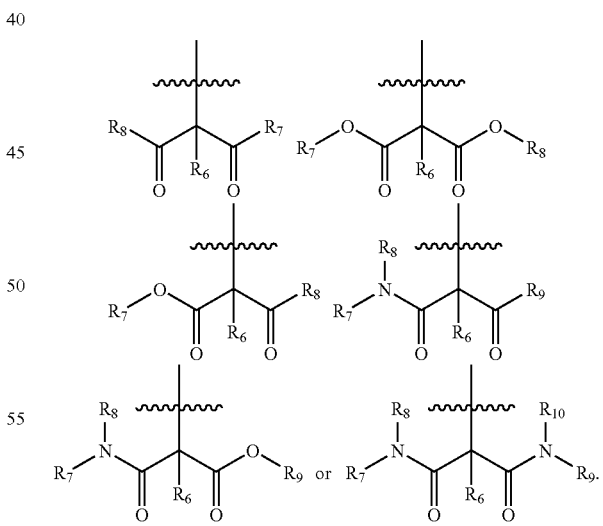

Also provided are compounds and salts of Formula I in which R is (iii) a 5-membered heteroaryl group having at least one nitrogen ring member, and 0, 1, or 2 additional ring members independently chosen from N, O, and S, wherein the 5-membered heteroaryl group is attached via a nitrogen atom and is substituted with 0 to 3 substituents independently chosen from halogen, hydroxy, amino, cyano, C$_1$-C$_4$alkyl, $C_1$-$C_4$alkoxy, mono- and di-($C_1$-$C_4$alkyl)amino, $C_1$-$C_2$haloalkyl, and $C_1$-$C_2$haloalkoxy. In certain of these embodiments R is pyrrolyl, imidazolyl, thiazolyl, oxazolyl, or isoxazolyl, each of which is attached via a nitrogen atom and substituted with 0 to 3 substituents independently chosen from halogen, hydroxy, amino, cyano, C1-C2alkyl, C1-C2alkoxy, mono- and di-(C1-C2alkyl)amino, trifluoromethyl, and trifluoromethoxy.

Within certain embodiments the protonated form, RH, of the weak nucleophile, R, has a PKa relative to water of 8 to 20. In certain preferred embodiments RH exhibits a PKa relative to water of 13 to 18.

The $R_6$, $R_7$, $R_8$, $R_9$, and $R_{10}$ Variables

Compounds and salts of Formula I are provided herein in which $R_6$, $R_7$, $R_8$, $R_9$, and $R_{10}$ are independently hydrogen, or $C_1$-$C_8$alkyl, $C_2$-$C_4$alkanoyl, or ($C_3$-$C_7$cycloalkyl)$C_0$-$C_2$alkyl, each of which is substituted with from 0 to 2 substituents independently chosen from halogen, hydroxy, amino, cyano, C1-C4alkyl, C1-C4alkoxy, mono- and di-(C1-C4alkyl)amino, C1-C2haloalkyl, and C1-C2haloalkoxy.

Within certain embodiments R6, R7, R8, R9, and R10 are independently hydrogen or C1-C4alkyl.

Pharmaceutical Preparations

A pharmaceutical composition, comprising a compound or form thereof of Formula I, together with at least one pharmaceutically acceptable carrier or excipient is provided herein.

In certain embodiments the pharmaceutical composition is formulated as an injectable fluid, an aerosol, a cream, a gel, a tablet, a pill, a capsule, a syrup, ophthalmic solution, or a transdermal patch.

Compounds, salts, and any other pharmaceutically acceptable forms of the invention can be administered as the neat chemical, but are preferably administered as a pharmaceutical composition or formulation. Accordingly, the invention provides pharmaceutical formulations comprising a compound or pharmaceutically acceptable form of Formula I, together with one or more pharmaceutically acceptable carriers, excipients, adjuvants, diluents, or other ingredients.

Pharmaceutical carriers must be of sufficiently high purity and sufficiently low toxicity to render them suitable for administration to the animal being treated. The carrier can be inert or it can possess pharmaceutical benefits. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of one or more of the compounds of Formula I including pharmaceutically acceptable salts, esters or other derivatives thereof are mixed with a suitable pharmaceutical carrier, excipient, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN, or cyclodextrin carriers. Derivatives of the compounds, such as salts of the compounds or prodrugs of the compounds may also be used in formulating effective pharmaceutical compositions.

Upon mixing or addition of the compound(s) of the invention, the resulting mixture may be a solution, suspension, emulsion, or the like. The form of the resulting mixture depends upon a number of factors, including the intended mode of administration and the solubility of the compound in the chosen carrier or vehicle. The effective concentration sufficient for ameliorating the symptoms of the disease, disorder, or condition treated and may be empirically determined.

Certain compounds described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous and oily suspensions, dispersible powders or granules, emulsions, hard or soft capsules, and syrups and elixirs. Compositions intended for oral use may be prepared according to any method known in the art for the manufacture of pharmaceutical compositions. Such compositions may contain one or more agents, such as sweetening agents, flavoring agents, coloring agents and preserving agents, in order to provide pharmaceutically elegant and palatable preparations. Oral formulations contain between 0.1 and 99% of a compound of the invention and usually at least about 5% (weight %) of a compound of the present invention. Some embodiments contain from about 25% to about 50% or from 5% to 75% of a compound of invention.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Orally Administered Liquids Formulations

Certain compounds described herein can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of compounds described herein may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Enteric Coated Dosage Forms

Enteric coated formulations, which protect the pseudobase benzo[c]phenanthridine against conversion to the parent benzo[c]phenanthridinium alkaloid, are also particularly desirable.

Preferably the enteric coating is a coating that prevents release of the active agent until the dosage form reaches the small intestine. Enteric coated dosage forms comprise a compound of Formula I coated with an enteric polymer. The enteric polymer should be non-toxic and is predominantly soluble in the intestinal fluid, but substantially insoluble in the gastric juices. Examples include polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L), which is an anionic copolymer based on methacrylate and available as a powder (also known as methacrylic acid copolymer, type A NF, methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin bearing carboxyl groups. The methacrylic acid: acrylic acid ethyl ester 1:1 copolymer solid substance of the acrylic dispersion sold under the trade designation "EUDRAGIT L-100-55" may be suitable.

One embodiment provides an enteric coated dosage form comprising a compound of Formula I, coated with an enteric coating that comprises an enteric polymer of the methacrylic type and optionally a plasticizer. The enteric coating can contain about 40 wt % to about 95 wt % enteric polymer (e.g., EUDRAGIT L30D-55) and about 5 wt % to about 60 wt % plasticizer (e.g., triethyl citrate, polyethylene glycol) based on the total weight of the enteric coating. The relative proportions of ingredients, notably the ratio methacrylic polymer to plasticizer can be varied according to a methods known to those of skill in the art of pharmaceutical formulation.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The compound or compounds of the invention, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least about 90% by weight of the total composition. Preferred carriers for parenteral administration include propylene glycol, ethyl oleate, pyrrolidone, ethanol, and sesame oil.

Suppositories

Certain compounds described herein may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Topical Formulations

Certain compounds described herein may be formulated for local or topical application, such as for topical application to the skin and mucous membranes, such as in the eye, in the form of gels, creams, and lotions and for application to the eye. Topical compositions of the present invention may be in any form including, for example, solutions, creams, ointments, gels, lotions, milks, cleansers, moisturizers, sprays, skin patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, iso-propyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, isobutane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Certain compounds described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorption enhancers.

Pharmaceutical compositions containing a compound of Formula I may also contain additional active agents that can be chosen from a wide variety of molecules, which can function in different ways to enhance the therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds, salts, or other pharmaceutically acceptable forms thereof, of Formula I in a container and optionally containing instructions for using the composition to treat a mammal suffering from a disease or disorder responsive to treatment with a pseudobase benzo[c]phenanthridines and/or a disease or disorder responsive to treatment with a benzo[c]phenanthridinium alkaloid or prevent such a disease or disorder in a patient. Preferably the packaged pharmaceutical formulation contains instructions for using the composition to treat a patient suffering from a microbial infection or a disease or disorder in which protein kinase C activity, topoisomerase I, and/or II activity, or cytotoxicity is implicated.

Preferably the mammal is a human patient, but may be any mammal, for example a domesticated companion animal, such as a cat or dog, or a livestock animal, such as a pig, horse, or cow.

Within certain embodiments the packaged pharmaceutical composition includes instructions for using the composition to treat a patient suffering from cancer, gum disease, a microbial infection, viral infection, fungal infection, AIDS, bipolar disorder, or schizophrenia.

The invention includes providing prescribing information; for example, to a patient or health care provider, or as a label in a packaged pharmaceutical formulation. Prescribing information may include, for example, efficacy, dosage and administration, contraindication and adverse reaction information pertaining to the pharmaceutical formulation.

In all of the foregoing the compounds of the invention can be administered alone, as mixtures, or in combination with other active agents.

Methods of Treatment

Within certain aspects, the methods for treating or inhibiting the development of a microbial infection, a fungal infection, a viral infection, a disease or disorder responsive to protein kinase C, topoisomerase I, and/or II modulation. In other words, therapeutic methods provided herein may be used to treat a patient already afflicted with a disease, or may be used to prevent or delay the onset of such a disease in a patient who is free of detectable microbial infection, fungal infection or a disease that is associated with protein kinase C, topoisomerase I, and/or II modulation. Modulation refers to inhibition or activation. Certain preferred compounds of Formula I described herein are potent inhibitors of protein kinase C, topoisomerase I, and/or topoisomerase II.

Diseases and disorders responsive to protein kinase C, topoisomerase I and/or topoisomerase II modulation include, but are not limited to disorders associated with diabetes, including diabetic vascular disease, diabetic macular edema, and diabetic neuropathy; cancer, including leukemia, particularly acute myeloid leukemia, non-small cell lung cancer, and cervical cancer; inflammatory conditions, including allergic inflammation, allergic skin disease, allergic respiratory disease, and asthma; neuropsychiatric disorders, including bipolar disorder, attention deficit disorder, senile dementia, the negative symptoms of schizophrenia, anxiety disorder, post-traumatic stress disorder, major depressive disorder, and Alzheimer's dementia; and neuropathic pain, particularly thermal hyperalgesia; These conditions may be diagnosed and monitored using criteria that have been established in the art.

The invention provides a method of treating a mammal, having a microbial infection, fungal infection, or disease or disorder responsive to protein kinase C, topoisomerase I, and/or topoisomerase II modulation comprising administering an effective amount of a compound of Formula I to the mammal. The mammal will typically be a human patient, but methods of treating domesticated companion animals (pets, such as dogs) and livestock animals are also within the scope of the invention.

Frequency of dosage may vary depending on the compound used and the particular disease to be treated or prevented. In general, for treatment of most disorders, a dosage regimen of 4 times daily or less is preferred. For the treatment of neuropsychiatric disorders, a dosage regimen of 1 or 2 times daily is particularly preferred. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease in the patient undergoing therapy. In certain embodiments, administration at meal times is preferred. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

EXAMPLES

Example 1

Conversion of Benzo[c]Phenanthridinium to its Pseudobase Benzo[c]Phenanthridine

Water forms an unstable adduct with chelerythrine that can be seen in NMR studies. 6-Methoxy-5,6-dihydrochelerytherine and 6-ethoxy-5,6,-dihydrochelerytherine have been reported as byproducts formed during the Sanguinaria extract process involving methanol and ethanol extraction of these alkaloids from blood root.

Pseudobase benzo[c]phenanthridines form when a weak nucleophile that can establish an equilibrium that between the pseudobase phenanthrdine and parent benzo[c]phenanthridinium in the biological medium, is added to a solution of the parent benzo[c]phenanthridinium in a non-polar solvent. Typically the weak nucleophile has a PKa of 10-20 relative to water.

The Addition is Depicted in Scheme 1.

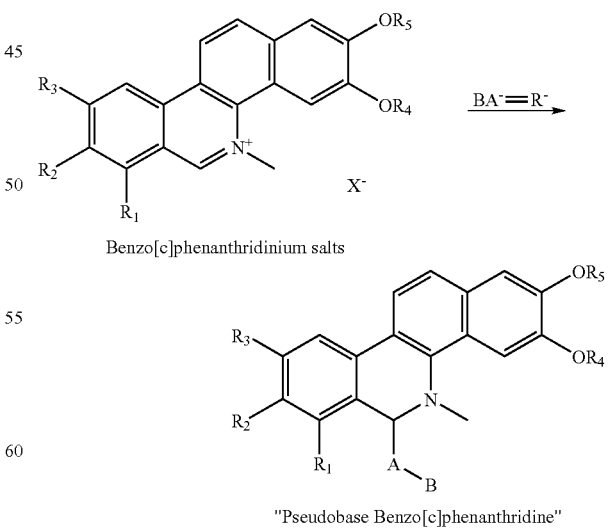

Method of Preparation:

Sodium hydride (1.2 equivalents based on the nucleophile RH) is added to a solution containing the nucleophile (RH) in tetrahydrofuran (THF) or N-Methylpyrrollidone (NMP) at 0° C. and allowed to warm to room temperature. The solution is then stirred for 1 hour. A solution of the phenanthridinium alkaloid (0.2-1 mole equivalent based on the nucleophiles RH)) in methylene chloride is added and the mixture is stirred for 4-6 hours or until the color disappears (assuming the starting nucleophile solution was colorless). Water is added and desired product extracted with ethyl acetate of dichloromethane. The organic phase is evaporated under reduced pressure and chromatographed (ethyl acetate-methanol, with or without 0.5% triethylamine or crystallized to provide the pure pseudobase benzo [c]phenanthridine.

Example 2

Additional Pseudobase Benzo[c]Phenanthridines

TABLE II

| CMP. # | STRUCTURE | Name |
|---|---|---|
| 1 | 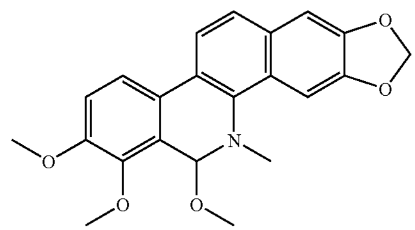 [SMILES: COc1ccc2c(c1OC)C(OC)N(C)c1c-2ccc2cc3c(cc12)OCO3] | 6-Methoxy-5,6-dihydrochelerythrine |
| 2 | 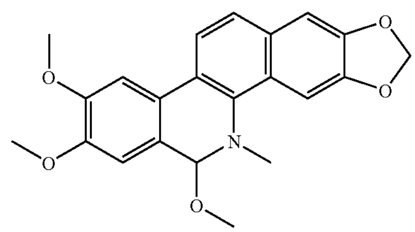 [SMILES: COc1cc2c(cc1OC)C(OC)N(C)c1c-2ccc2cc3c(cc12)OCO3] | 6-methoxy-5,6-dihydronitidine |
| 3 | 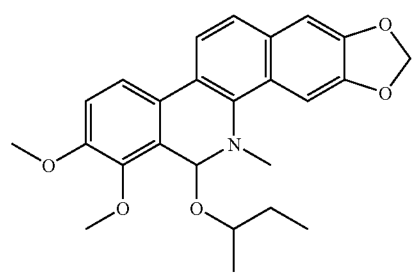 [SMILES: CCC(C)OC1c2c(ccc(OC)c2OC)-c2ccc3cc4c(cc3c2N1C)OCO4] | 6-(2-butoxy)-5,6-dihydrochelerythrine |
| 4 | 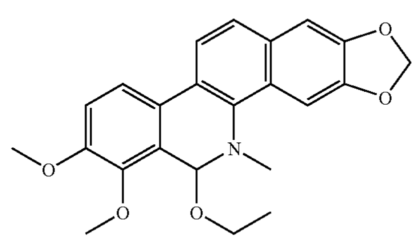 [SMILES: CCOC1c2c(ccc(OC)c2OC)-c2ccc3cc4c(cc3c2N1C)OCO4] | 6-Ethoxy-5,6-dihydrochelerythrine (Atarine) |
| 5 | 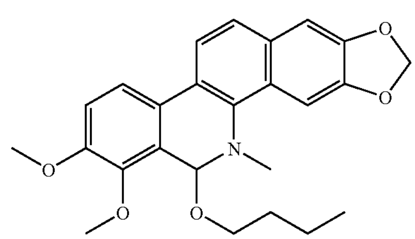 [SMILES: CCCCOC1c2c(ccc(OC)c2OC)-c2ccc3cc4c(cc3c2N1C)OCO4] | 6-butoxy-5,6-dihydrochelerythrine |

TABLE II-continued

| CMP. # | STRUCTURE | Name |
|---|---|---|
| 6 | 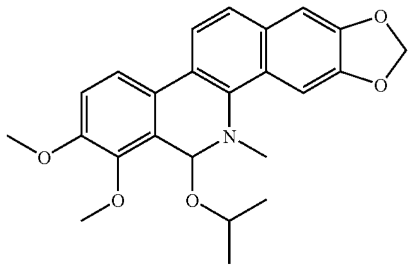 [SMILES: COc1ccc2c(c1OC)C(OC(C)C)N(C)c1c-2ccc2cc3c(cc12)OCO3] | 6-Isopropoxy-5,6-dihydrochelerythrine |
| 7 | 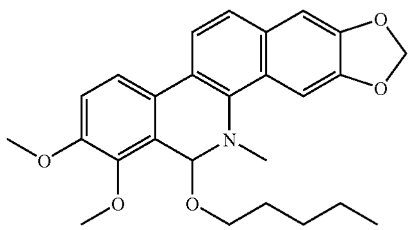 [SMILES: CCCCCOC1c2c(ccc(OC)c2OC)-c2ccc3cc4c(cc3c2N1C)OCO4] | 6-pentoxy-5,6-dihydrochelerythrine |
| 8 | 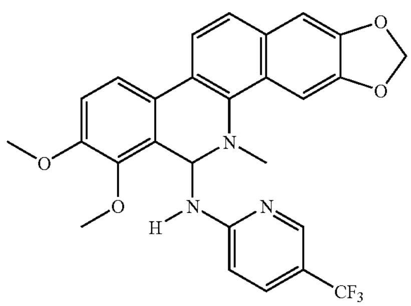 [SMILES: COc1ccc2c(c1OC)C(Nc1ccc(C(F)(F)F)cn1)N(C)c1c-2ccc2cc3c(cc12)OCO3] | (5-(trifluoromethyl)pyridin-2-yl)-5,6-dihydrochelerythrine |
| 9 | 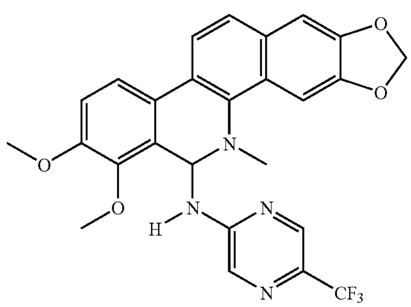 [SMILES: COc1ccc2c(c1OC)C(Nc1cnc(C(F)(F)F)cn1)N(C)c1c-2ccc2cc3c(cc12)OCO3] | N-(5-(trifluoromethyl)pyrazin-2-yl)-5,6-dihydrochelerythrine-6-amine |
| 10 | 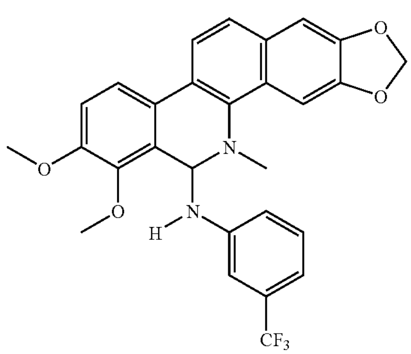 [SMILES: COc1ccc2c(c1OC)C(Nc1cccc(C(F)(F)F)c1)N(C)c1c-2ccc2cc3c(cc12)OCO3] | N-(3-(trifluoromethyl)phenyl)-5,6-dihydrochelerythrine-6-amine |

TABLE II-continued

| CMP. # | STRUCTURE | Name |
|---|---|---|
| 11 | 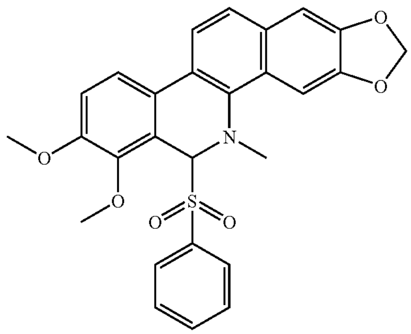 [SMILES: COc1ccc2c(c1OC)C(S(=O)(=O)c1ccccc1)N(C)c1c-2ccc2cc3c(cc12)OCO3] | 6-(phenylsulfonyl)-5,6-dihydrochelerytherine |
| 12 | 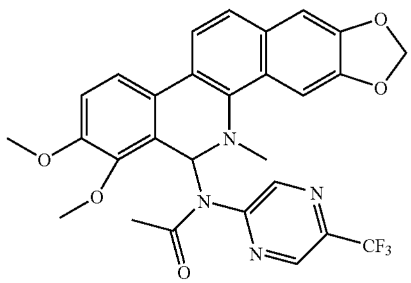 [SMILES: COc1ccc2c(c1OC)C(N(C(C)=O)c1cnc(C(F)(F)F)cn1)N(C)c1c-2ccc2cc3c(cc12)OCO3] | 5,6-dihydrocheleryth rine-6-yl)-N-(5-(trifluoromethyl)pyrazin-2-yl)acetamide |
| 13 | 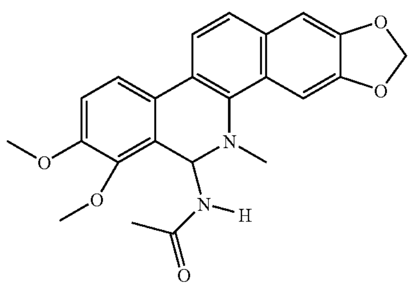 [SMILES: COc1ccc2c(c1OC)C(NC(C)=O)N(C)c1c-2ccc2cc3c(cc12)OCO3] | N--5,6-dihydrochelerythrine-6-yl)-acetamide |
| 14 | 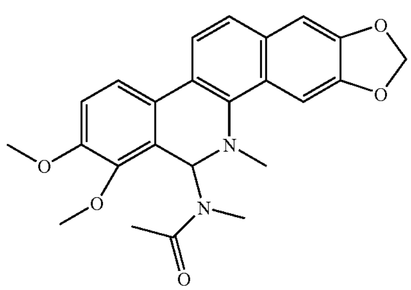 [SMILES: COc1ccc2c(c1OC)C(N(C)C(C)=O)N(C)c1c-2ccc2cc3c(cc12)OCO3] | N--5,6-dihydrochelerythrine-6-yl)-N-methylacetamide |
| 15 | 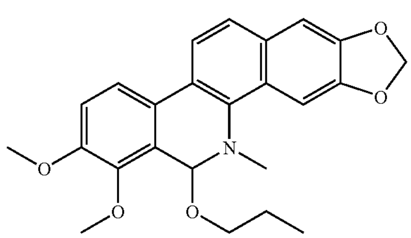 [SMILES: CCCOC1c2c(ccc(OC)c2OC)-c2ccc3cc4c(cc3c2N1C)OCO4] | 6-propoxy-5,6-dihydrochelerythrine |

TABLE II-continued

| CMP. # | STRUCTURE | Name |
|---|---|---|
| 16 | 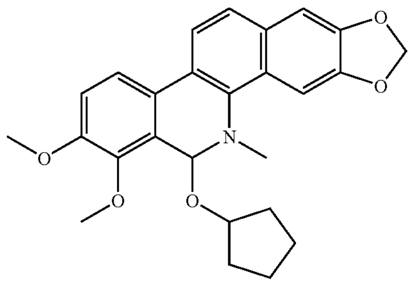 [SMILES: COc1ccc2c(c1OC)C(OC1CCCC1)N(C)c1c-2ccc2cc3c(cc12)OCO3] | 6-(cyclopentyloxy)-5,6-dihydrochelerythrine |
| 17 | 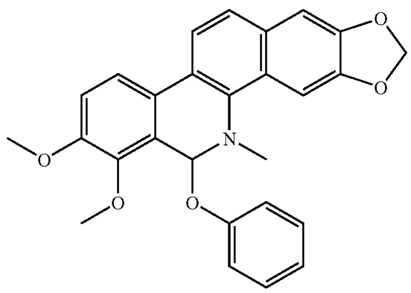 [SMILES: COc1ccc2c(c1OC)C(Oc1ccccc1)N(C)c1c-2ccc2cc3c(cc12)OCO3] | 6-Phenoxy-5,6-dihydrochelerythrine |
| 18 | 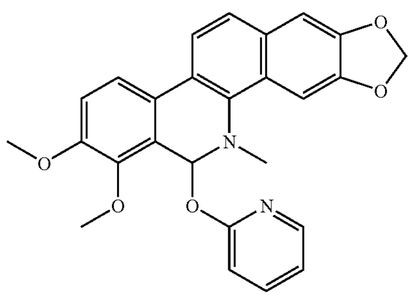 [SMILES: COc1ccc2c(c1OC)C(Oc1ccccn1)N(C)c1c-2ccc2cc3c(cc12)OCO3] | 6-(pyridin-2-yloxy)-5,6-dihydrochelerythrine |
| 19 | 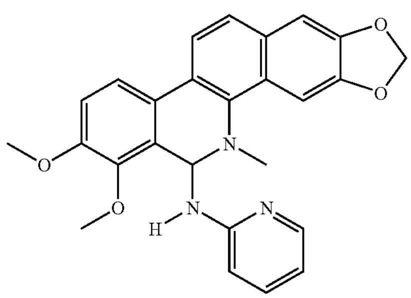 [SMILES: COc1ccc2c(c1OC)C(Nc1ccccn1)N(C)c1c-2ccc2cc3c(cc12)OCO3] | 6-N-(pyridin-2-yl)-5,6-dihydrochelerythrine |
| 20 | 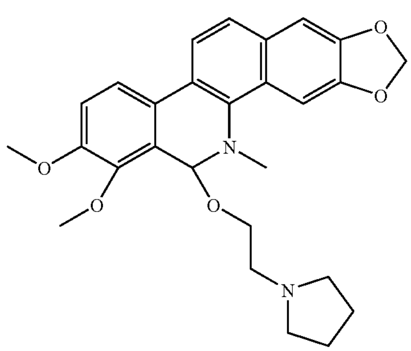 [SMILES: COc1ccc2c(c1OC)C(OCCN1CCCC1)N(C)c1c-2ccc2cc3c(cc12)OCO3] | 6-(2-(pyrrolidin-1-yl)ethoxy)-5,6-dihydrochelerythrine |

TABLE II-continued

| CMP. # | STRUCTURE | Name |
|---|---|---|
| 21 | 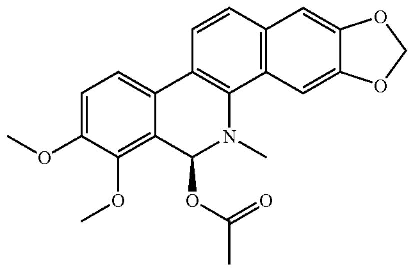 [SMILES: COc1ccc2c(c1OC)[C@H](OC(C)=O)N(C)c1c-2ccc2cc3c(cc12)OCO3] | 5,6-dihydrochelerythrine-6-yl acetate |
| 22 | 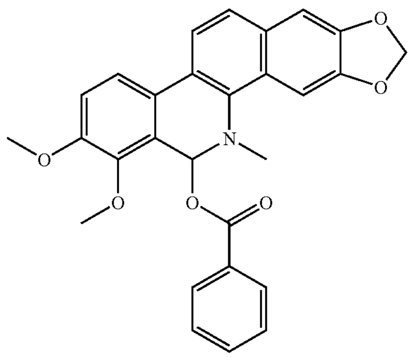 [SMILES: COc1ccc2c(c1OC)C(OC(=O)c1ccccc1)N(C)c1c-2ccc2cc3c(cc12)OCO3] | 5,6-dihydrochelerythrine-6-yl benzoate |
| 23 | 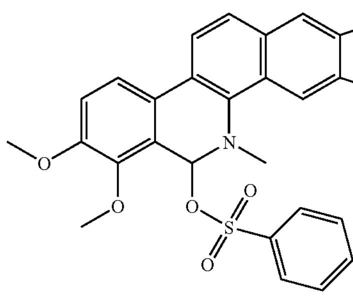 | 5,6-dihydrochelerythrine-6-yl benzenesulfonate |
| 24 | 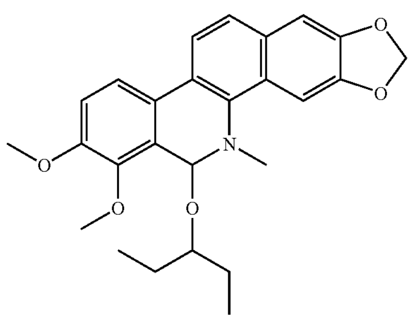 [SMILES: CCC(CC)OC1c2c(ccc(OC)c2OC)-c2ccc3cc4c(cc3c2N1C)OCO4] | 6-(3-pentoxy)-5,6-dihydrochelerytherine |
| 25 | 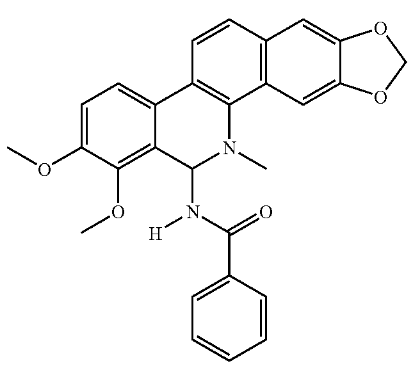 [SMILES: COc1ccc2c(c1OC)C(NC(=O)c1ccccc1)N(C)c1c-2ccc2cc3c(cc12)OCO3] | N-(5,6-dihydrochelerythrine-6-yl)benzamide |

TABLE II-continued

| CMP. # | STRUCTURE | Name |
|---|---|---|
| 26 | 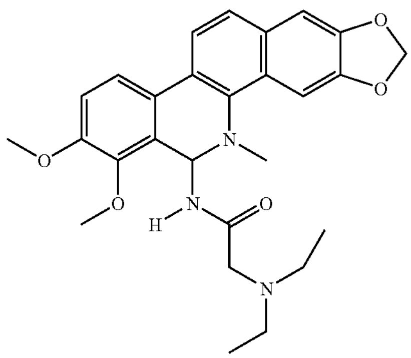 [SMILES: CCN(CC)CC(=O)NC1c2c(ccc(OC)c2OC)-c2ccc3cc4c(cc3c2N1C)OCO4] | 2-(diethylamino)-N-(5,6-dihydrochelerythrine-6-yl)acetamide |
| 27 | 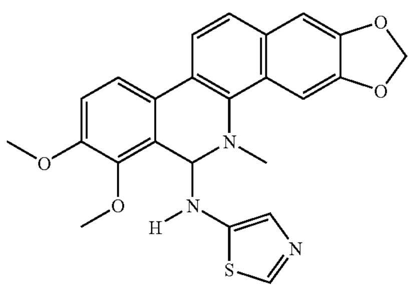 [SMILES: COc1ccc2c(c1OC)C(Nc1cncs1)N(C)c1c-2ccc2cc3c(cc12)OCO3] | N-(thiazol-5-yl)-5,6-dihydrochelerythrine-6-amine |
| 28 | 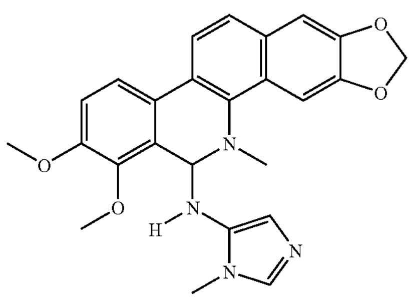 [SMILES: COc1ccc2c(c1OC)C(Nc1cncn1C)N(C)c1c-2ccc2cc3c(cc12)OCO3] | 1-N-(1-methyl-1H-imidazol-5-yl)-5,6-dihydrochelerythrine-6-amine |
| 29 | 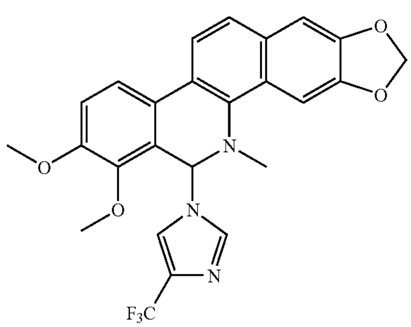 [SMILES: COc1ccc2c(c1OC)C(n1cnc(C(F)(F)F)c1)N(C)c1c-2ccc2cc3c(cc12)OCO3] | 6-(4-(trifluoromethyl)-1H-imidazol-1-yl)-5,6-dihydrochelerythrine |
| 30 | 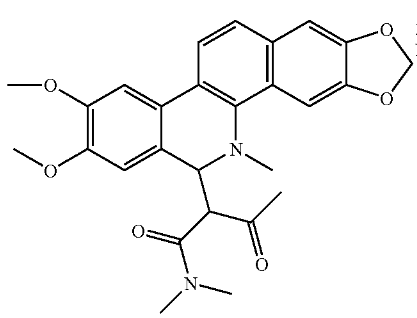 [SMILES: COc1cc2c(cc1OC)C(C(C(C)=O)C(=O)N(C)C)N(C)c1c-2ccc2cc3c(cc12)OCO3] | 2-(5,6-dihydronitidine-6-yl)-N,N-dimethyl-3-oxobutanamide |

TABLE II-continued

| CMP. # | STRUCTURE | Name |
|---|---|---|
| 31 | 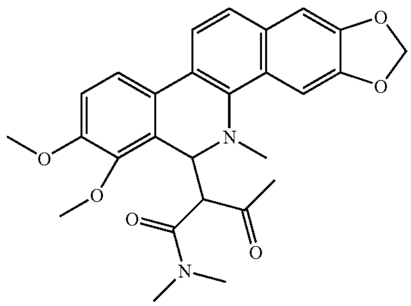 [SMILES: COc1ccc2c(c1OC)C(C(C(C)=O)C(=O)N(C)C)N(C)c1c-2ccc2cc3c(cc12)OCO3] | 2-(5,6-dihydrochelerythrine-6-yl)-N,N-dimethyl-3-oxobutanamide |

Compounds of Formula 1, 2, or 3, are also prepared by the method given in Scheme I,

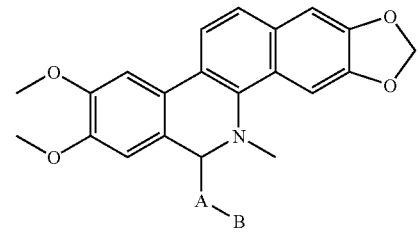

Formula 1

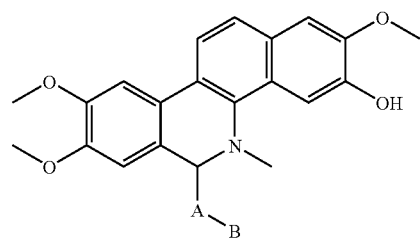

Formula 2

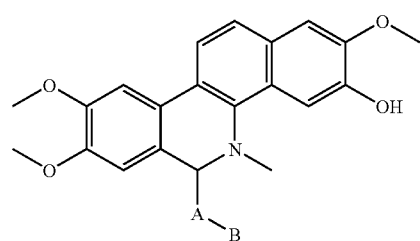

Formula 3

Wherein -A is —O—, —NH—, —SO$_2$—, —O(C═O)—, —O(SO$_2$)—, or —NH(C═O)— and B is —CH$_3$, —CH(CH$_3$)(CH$_2$CH$_3$), —CH$_2$CH$_3$, —(CH$_2$)$_2$CH$_3$, —(CH$_2$)$_3$CH$_3$, —(CH$_2$)$_4$CH$_3$, —CH(CH$_3$)$_2$, 3-pentyl, cyclopentyl, phenyl, pyrid-2-yl, 5-(trifluoromethyl)pyridin-2-yl, 5-(trifluoromethyl)pyrazin-2-yl, 2-(pyrrolidin-1-yl)ethoxy, 3-(trifluoromethyl)phenyl, 1-methyl-1H-imidazol-5-yl, or thiazol-5-yl.

Compounds of Formula 4, 5, or 6, are also prepared by the method given in Scheme I,

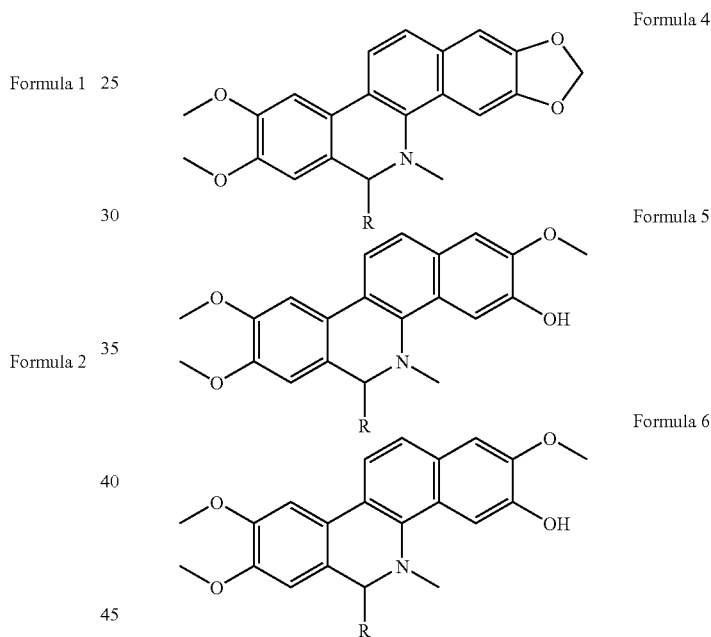

Wherein R is

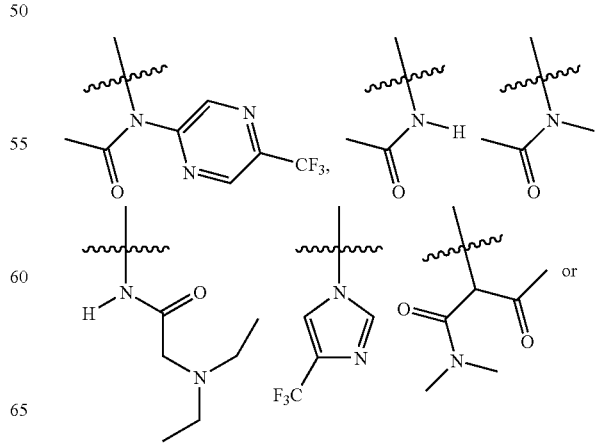

-continued

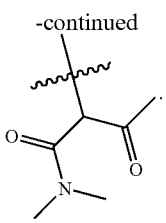

Example 3

Permeability of Caco-2 Monolayers to Pseudobase Benzo[c]Phenanthridinium Derivatives Passive diffusion across Caco-2 cell monolayers may used to assess cell membrane permeability of pseudobase benzo[c]phenanthridines relative to the parent phenanthridinium alkaloids. Caco-2 cells are available pre-plated in 24-well Corning Costar Transwell® filters from In Vitro Technologies, Cantonsville, Md. Test compounds are diluted in THF and added to culture media containing 10% FBS. The final test compound concentration is 1 microgram/ml. The test compound/culture media mixture is added to the upper well of the Caco-2 cell transwell plate, and the plates are incubated with gentle shaking at 37° C., 5%) $CO_2$. Test compound concentration in the lower well of the transwell plate is determined by LC/Ms 2, 4, 6, and 4 hours after incubation and compared to control. For each pseudobase benzo[c]phenanthridine compound the control is the parent benzo[c]phenanthridinium alkaloid.

Example 4

Antimicrobial Activity of Pseudobase Benzo[c]Phenanthridines

The antimicrobial activity of the compounds described herein may be evaluated by the following visual minimum inhibitory concentration (MIC) assay. This assay determines the minimum concentration of compound required to inhibit growth of a bacterial strain.

Test compounds are dissolved in non-polar solvent and diluted 1:50 in Mueller-Hinton II broth (Becton-Dickinson) to produce a 256 µg/ml stock solution. The compound solution is serially diluted in Mueller-Hinton II broth in a 96-well microtiter plate. After the compounds are diluted, a 50 µl aliquot of the test organism (~1×10$^6$ cfu/mL) is added to each well of the microtiter plate. The final test concentrations range from 0.125-128 µg/mL. Inoculated plates are incubated in ambient air at 37° C. for 18 to 24 hours. The organisms selected for testing include *S. aureus* and *E. coli* (laboratory strains may be purchased from American Type Culture Collection, Manassas, Va.). The minimum inhibitory concentration (MIC) is determined as the lowest concentration of compound that inhibits visible growth of the test organism.

Example 5

Topoisomerase I Inhibition Assay

The following assay, essentially that described by Prado et al, *Bioorg. Med. Chem.* 12: 3943-3953 (2004) may be used to observe the topoisomerase I activity inhibition by pseudobase benzo[c]phenanthridines. Supercoiled DNA migrates more slowly than DNA which has been uncoiled by active topoisomerase I. Thus a higher level of slow migrating "supercoiled" DNA relative to control indicates topoisomerase I inhibition.

Recombinant topoisomerase I protein is produced and purified from baculovirus infected Sf9 cells by methods well known in the art. Supercoiled pKMp27 DNA (0.4 micrograms) is incubated with 4 units topoisomerase I at 37° C. for 1 hour in relaxation buffer (50 mM Tris pH 7.8, 50 mM KCl, 10 mM $MgCl_2$, 1 mM Dithiothreitol, 1 mM EDTA) in the presence of varying concentrations of a compound of Formula I or a parent benzo[c]phenanthridinium alkaloid of such compound (control). Reactions are terminated by adding SDS to 0.25% and proteinase K to 250 micrograms/mL. DNA samples are then added to electrophoresis dye mixture (3 microliters) and electrophoresed in an ethidium-containing 1% agarose gel at room temperature for about 2 hours at 120V. Gels are washed and photographed under UV light.

What is claimed is:

1. A method of treating a patient suffering from bipolar disorder, attention deficit disorder, or schizophrenia comprising administering an effective amount of a compound or pharmaceutically acceptable salt of Formula I to the patient, wherein Formula I is

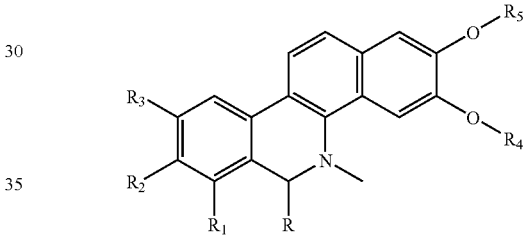

in which:

$R_1$ and $R_2$ are each independently hydrogen, halogen, hydroxyl, $C_1$-$C_3$alkyl, $C_1$-$C_6$alkoxy, or $C_1$-$C_6$alkylester; or $R_1$ and $R_2$ are joined by a —O—$CH_2$—O— group;

$R_3$ is hydrogen or methoxy;

$R_4$ and $R_5$ are independently methyl or hydrogen; or $R_4$ and $R_5$ are joined to form a 5-membered heterocyclic ring containing no additional heteroatoms; and R is (i) a group of the formula -AB, where A is —$NR_6$—, —O—, —$NR_6$(C=O)—, —S(O)$_m$—, —$CH_2$C(=O)—, —S(O)$_m$$NR_6$—, —$NR_6$S(O)$_m$—, —OS(O)$_m$—, —$NR_6$(S=O)$NR_7$—, —O(C=O)—, or —$NR_6$(C=O)$NR_7$—, where m is 0, 1, or 2;

—B is (phenyl)$C_0$-$C_2$alkyl, ($C_3$-$C_7$cycloalkyl)$C_0$-$C_2$alkyl, (pyrrolidinyl)$C_0$-$C_2$alkyl, (piperidinyl)$C_0$-$C_2$alkyl, (piperazinyl)$C_0$-$C_2$alkyl, (morpholinyl)$C_0$-$C_2$alkyl, (pyridyl)$C_0$-$C_2$alkyl, (thienyl)$C_0$-$C_2$alkyl, (pyrrolyl)$C_0$-$C_2$alkyl, (furanyl)$C_0$-$C_2$alkyl, (imidazolyl)$C_0$-$C_2$alkyl, (thiazolyl)$C_0$-$C_2$alkyl, (pyrimidinyl)$C_0$-$C_2$alkyl, or (pyrazinyl)$C_0$-$C_2$alkyl, each of which is substituted with from 0 to 4 substituents independently chosen from halogen, hydroxyl, amino, cyano, $C_1$-$C_4$alkyl, $C_1$-$C_4$alkoxy, mono- and di-($C_1$-$C_4$alkyl)amino, $C_1$-$C_2$haloalkyl, or $C_1$-$C_2$haloalkoxy;

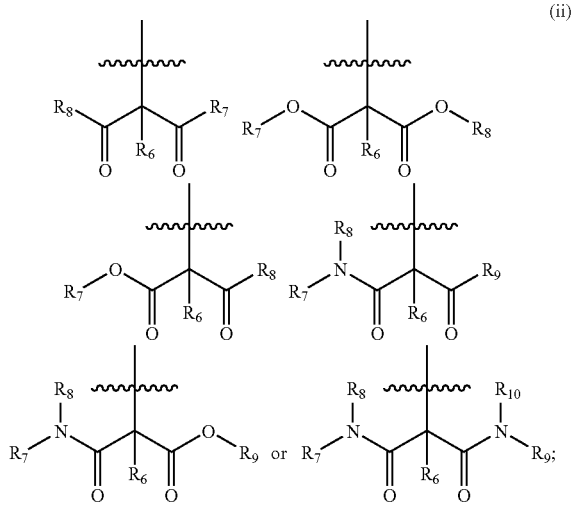

(ii)

(iii) a 5-membered heteroaryl group having at least one nitrogen ring member, and 0, 1, or 2 additional ring members independently selected from the group consisting of N, O, and S, wherein the 5-membered heteroaryl group is attached via a nitrogen atom and is substituted with 0 to 3 substituents independently selected from the group consisting of halogen, hydroxyl, amino, cyano, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy; or (iv) a 5- or 6-membered heterocycloalkyl group linked via a nitrogen atom, wherein the heterocycloalkyl is substituted with from 0 to 4 substituents independently selected from the group consisting of halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, $C_1$-$C_2$haloalkyl, $C_1$-$C_2$haloalkoxy, and 5- and 6-membered heterocycloalkyl; where $R_6$, $R_7$, $R_8$, $R_9$, and $R_{10}$ are each independently hydrogen, or $C_1$-$C_8$alkyl, $C_2$-$C_8$alkenyl, $C_2$-$C_8$alkynyl, $C_2$-$C_4$alkanoyl, ($C_3$-$C_{10}$cycloalkyl)$C_0$-$C_8$alkyl, (heterocycloalkyl)$C_0$-$C_8$alkyl, or phenyl each of which is substituted with from 0 to 4 substituents independently selected from the group consisting of halogen, hydroxyl, amino, cyano, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

* * * * *